United States Patent
Mak et al.

(10) Patent No.: US 11,487,916 B2
(45) Date of Patent: Nov. 1, 2022

(54) METHOD AND SYSTEM FOR BRACE DESIGNING

(71) Applicant: Telefield Medical Imaging Limited, Hong Kong (HK)

(72) Inventors: Takman Mak, Hong Kong (HK); Yongping Zheng, Hong Kong (HK)

(73) Assignee: Telefield Medical Imaging Limited, Hong Kong (HK)

( * ) Notice: Subject to any disclaimer, the term of this patent is extended or adjusted under 35 U.S.C. 154(b) by 539 days.

(21) Appl. No.: 16/319,471

(22) PCT Filed: Jun. 9, 2017

(86) PCT No.: PCT/CN2017/087683
§ 371 (c)(1),
(2) Date: Jan. 21, 2019

(87) PCT Pub. No.: WO2018/019034
PCT Pub. Date: Feb. 1, 2018

(65) Prior Publication Data
US 2019/0243934 A1    Aug. 8, 2019

(30) Foreign Application Priority Data
Jul. 25, 2016  (CN) .......................... 201610589134.0

(51) Int. Cl.
*G06G 7/48*  (2006.01)
*G06F 30/20*  (2020.01)
(Continued)

(52) U.S. Cl.
CPC ............... *G06F 30/20* (2020.01); *A61F 5/01* (2013.01); *G06F 30/00* (2020.01); *G06F 30/17* (2020.01);
(Continued)

(58) Field of Classification Search
CPC ........ A61F 2/5046; A61F 5/01; A61F 5/0104; G06F 30/00; G06F 2111/16; G06F 30/13;
(Continued)

(56) References Cited

U.S. PATENT DOCUMENTS

2010/0138193 A1* 6/2010 Summit ................. B33Y 50/00
703/1

OTHER PUBLICATIONS

Wolbrecht, Eric T., et al. "Control of a pneumatic orthosis for upper extremity stroke rehabilitation." 2006 International Conference of the IEEE Engineering in Medicine and Biology Society. IEEE, 2006.*

(Continued)

*Primary Examiner* — Rehana Perveen
*Assistant Examiner* — Nithya J. Moll (57) ABSTRACT

Method and system for brace designing. The method comprises the following steps: S1) fixing a subject requiring a brace; S2) acquiring skeletal image information of the subject; S3) determining an adjustment solution for implementing an adjustment with respect to the subject and a target state that is to be achieved ultimately; S4) adjusting the subject to alter the skeletal structure of the subject; S5) acquiring adjusted skeletal image information of the subject; S6) determining whether the skeleton of the subject has been adjusted to the target state; if yes, then terminating adjustment and entering step S7; if not, then returning to step S4; S7) acquiring the body surface three-dimensional shape of the subject having achieved the target state and recording information of the force applied by an adjusting head to the subject for use in manufacturing a corresponding brace; thus allowing the highly efficient designing of a brace.

8 Claims, 5 Drawing Sheets

(51) Int. Cl.
G06F 30/00 (2020.01)
G06F 30/17 (2020.01)
G06G 7/60 (2006.01)
A61F 5/01 (2006.01)
G06F 111/16 (2020.01)

(52) U.S. Cl.
CPC ..... G06G 7/60 (2013.01); *G05B 2219/40324* (2013.01); *G06F 2111/16* (2020.01)

(58) Field of Classification Search
CPC .......... G06F 30/17; G06F 30/20; G06F 3/011; G05B 2219/40324; G06G 7/60
See application file for complete search history.

(56) References Cited

OTHER PUBLICATIONS

Jun, Seungkook, et al. "Smart knee brace design with parallel coupled compliant plate mechanism and pennate elastic band spring." Journal of Mechanisms and Robotics 7.4 (2015): 041024.*

Cheung, Chung-Wai James, et al. "Freehand three-dimensional ultrasound system for assessment of scoliosis." Journal of Orthopaedic Translation 3.3 (2015): 123-133.*

Nie, Wen-Zhong, et al. "The patient-specific brace design and biomechanical analysis of adolescent idiopathic scoliosis." Journal of biomechanical engineering 131.4 (2009).*

Lou, E., et al. "A smart orthosis for the treatment of scoliosis." 2005 IEEE Engineering in Medicine and Biology 27th Annual Conference. IEEE, 2006.*

Gibson, Ian, and Gao Zhan. "Finite element simulation of the spine with haptic interface." Proceedings of the 2nd International Convention on Rehabilitation Engineering & Assistive Technology. 2008.*

Velasquez, Carlos A., et al. "Development of a flexible imaging probe integrated to a surgical telerobot system: Preliminary remote control test and probe design." 2012 4th IEEE RAS & EMBS International Conference on Biomedical Robotics and Biomechatronics (BioRob). IEEE, 2012.*

Li, Meng, et al. "Could clinical ultrasound improve the fitting of spinal orthosis for the patients with AIS?." European Spine Journal 21.10 (2012): 1926-1935.*

* cited by examiner

METHOD AND SYSTEM FOR BRACE DESIGNING

TECHNICAL FIELD

The present disclosure relates generally to technical field of medical device, particularly to a method and system for a medical device designing, and more particularly to a method and system for a brace designing.

BACKGROUND

When the human skeleton structure is locally deformed or damaged, a brace is often used outside the body in the process of intervention and treatment. Taking the scoliosis as an example, it has a high incidence in adolescents, if the diagnosis and treatment are not timely, the scoliotic curve will increase with the development of the adolescents and even lead to serious body deformity, which will not only affect the cardiopulmonary functions of the patients, but also cause serious damage to their mental health. For most patients with scoliosis, in order to avoid the deterioration of scoliosis, brace treatment is needed. The brace needs to produce orthopedic forces on the spine at different points so as to give the orthopedic treatment to the scoliosis. The scoliosis brace is generally worn for 23 hours every day. However, the long-term of continuous skin compression of the brace would cause skin pressure sores, while the reduced orthopedic force avoiding the skin compression would affect the orthopedic effect. Therefore, how to design a brace which can guarantee a good orthopedic effect and meanwhile avoid continuous skin compression for different patients has been a challenge for the professionals working in this area for a long time.

At present, there are many designing schemes for spinal brace in the world, but they are all similar. They usually include the following steps. Step 1, understand the adjustable degree of the scoliosis (detecting the adjustable degree of the scoliosis on the X-ray film after requesting the patient to bend their body left and right). Step 2, adjust the spine by a device and determine the adjustment degree from the appearance (the patient can be lying or standing, the device usually has several adjustable rods rest against both side of the torso). Step 3, obtain the three-dimensional shape of the human torso in the adjusted state (via a plaster mold casting method or a three-dimensional scanning method on the body surface). Step 4, manufacture and adjust the brace according to the obtained three-dimensional shape of the human torso combining with experience. Step 5, let the patient to wear the brace and make the corresponding fine adjustment (by changing the local shape of the brace, adding the pad to the local portion or changing the tightness) for obtaining the best effect. In order to achieve a good adjustment effect, an X-ray imaging is also used to obtain multiple X-ray images during the adjustment of the brace, but this method will give the patient a lot of harmful radiation. It can be seen that in the existing design methods, there are too many uncertain factors in the determination of the adjustment degree from the appearance, which makes it difficult to achieve the desired therapeutic effect of the obtained brace, to guarantee a good orthopedic effect and meanwhile to avoid continuous skin compression for different patients. Moreover, the fine adjustment process of the brace is very tedious. Accordingly, it is necessary to create a new method and system for the brace designing to overcome the above problems.

SUMMARY

The object of the present application is to provide a method and system for a brace designing, capable of designing a brace which can ensure a good orthopedic effect and meanwhile avoid continuous skin compression with a high efficiency, aiming at the technical problems in the prior art that there are too many uncertain factors in the determination of the adjustment degree from the appearance, which makes it difficult to achieve the desired therapeutic effect of the obtained brace, to guarantee a good orthopedic effect and meanwhile to avoid continuous skin compression for different patients and the fine adjustment process of the brace is very tedious.

In a first aspect, a method for a brace designing is provided, comprising following steps:

S1, fixing a subject requiring a brace via an adjustment device comprising one or more adjustment head provided with a force sensor;

S2, scanning the subject to obtain skeletal image information of the subject;

S3, determining an adjustment solution for implementing an adjustment with respect to the subject and a target state that is to be achieved ultimately according to the skeletal image information;

S4, adjusting the subject to change a skeletal structure of the subject by using the adjustment head according to the adjustment solution, and meanwhile detecting a magnitude, direction and distribution of a force applied to the subject by the adjustment head via the force sensor;

S5, scanning the subject to obtain adjusted skeletal image information of the subject;

S6, determining whether the skeletal structure of the subject has been adjusted to the target state according to the adjusted skeletal image information; if yes, terminating adjustment and proceeding to step S7, or else, returning to step S4;

S7), obtaining a body surface three-dimensional shape of the subject having achieved the target state, and recording information about the magnitude, direction and distribution of the force applied to the subject by the adjustment headland detected by the force sensor for manufacturing a corresponding brace.

The method for a brace designing according to the present application, further comprises a step SA implemented after the steps S4 but before the step S5: determining whether the magnitude of the force applied to the subject by the adjustment head and detected by the force sensor is larger than a targeted value; if yes, proceeding to step S7, or else, proceeding to step S5.

In the method for a brace designing according to the present application, the skeletal image information in step S2 is displayed in real time for giving reference to step S3.

In a first aspect, a system for a brace designing is provided, comprising:

an adjustment device for fixing a subject requiring a brace, comprising one or more adjustment head provided with a force sensor for detecting a magnitude, direction and distribution of a force applied to the subject by the adjustment head;

a scanning imaging device for scanning the subject to obtain adjusted skeletal image information of the subject;

a first calculation unit for reading, quantizing and calculating the skeletal image information for obtaining a corresponding current parameter and target parameter of the subject;

a second calculation unit for calculating an adjustment solution of the adjustment head for guiding an operator to adjust the subject by using the adjustment head, according to the current parameter, the target parameter, the magnitude, direction and distribution of the force applied to the subject by the adjustment head and detected by the force sensor;

a monitoring module for monitoring whether the current parameter is consistent with the target parameter; if yes, sending out a termination signal to prompt the operator to terminate the adjustment and obtain the body surface three-dimensional shape of the subject by using a body surface three-dimensional shape obtaining device, or else sending out an operation signal to prompt the operator to continue the adjustment.

The system for a brace designing according to the present application further comprises an alarm device for reading information about the magnitude of the force applied to the subject by the adjustment head and detected by the force sensor, and sending out an alarm signal to prompt the operator to terminate the adjustment when the magnitude of the force applied to the subject by the adjustment head and detected by the force sensor is larger than a targeted value.

In the system for a brace designing according to the present application, the adjustment head is controlled by a first mechanical device having a brake module for receiving the alarm signal, wherein the first mechanical device stops running when the brake module receives the alarm signal.

In the system for a brace designing according to the present application, the first mechanical device has a first numerical control module for receiving signals sent by the monitoring module, wherein when the first numerical control module receives the termination signal, the first mechanical device stops running, while when the first numerical control module receives the operation signal, the first mechanical device reads the adjustment solution calculated by the second calculation unit and controls the adjustment head to adjust the subject according to the adjustment solution.

In the system for a brace designing according to the present application, the scanning imaging device is controlled by a second mechanical device comprising a second numerical control module for receiving signals sent by the monitoring module; wherein when the second numerical control module receives the termination signal, the scanning imaging device stops running, while when the second numerical control module receives the operation signal, the second mechanical device controls the scanning imaging device to scan the subject for obtaining the skeletal image information of the subject.

In the system for a brace designing according to the present application, the body surface three-dimensional shape obtaining device obtains the body surface three-dimensional shape of the subject by obtaining a cross-sectional view of the subject and a spatial position of each cross-sectional view.

In the system for a brace designing according to the present application, the scanning imaging device comprises a flexible imaging probe attached to a body surface of the subject.

When implementing the method and system for a brace designing according to the present application, following beneficial effects can be obtained. The brace suitable for the corresponding subject can be designed efficiently and intelligently for the different subjects, and the designed brace can ensure a good orthopedic effect and meanwhile avoid continuous skin compression, thus seeking a valuable treatment time and ideal treatment effect for the patients.

The reference numerals include:

TABLE 1

| Adjustment device | 1 | Subject | 2 |
|---|---|---|---|
| Scanning imaging device | 3 | First calculation unit | 4 |
| Second calculation unit | 5 | Monitoring module | 6 |
| Body surface three-dimensional shape obtaining device | 7 | Alarm device | 8 |
| First mechanical device | 11 | Adjustment head | 12 |
| Force sensor | 13 | Fixing frame | 14 |
| Second mechanical device | 31 | | |

DETAILED DESCRIPTION OF THE PREFERRED EMBODIMENT

The embodiments of the present application are further illustrated with reference to the accompanying drawings and embodiments for a better understanding of the technical features, objects, and advantages of the present application.

Figure 1:
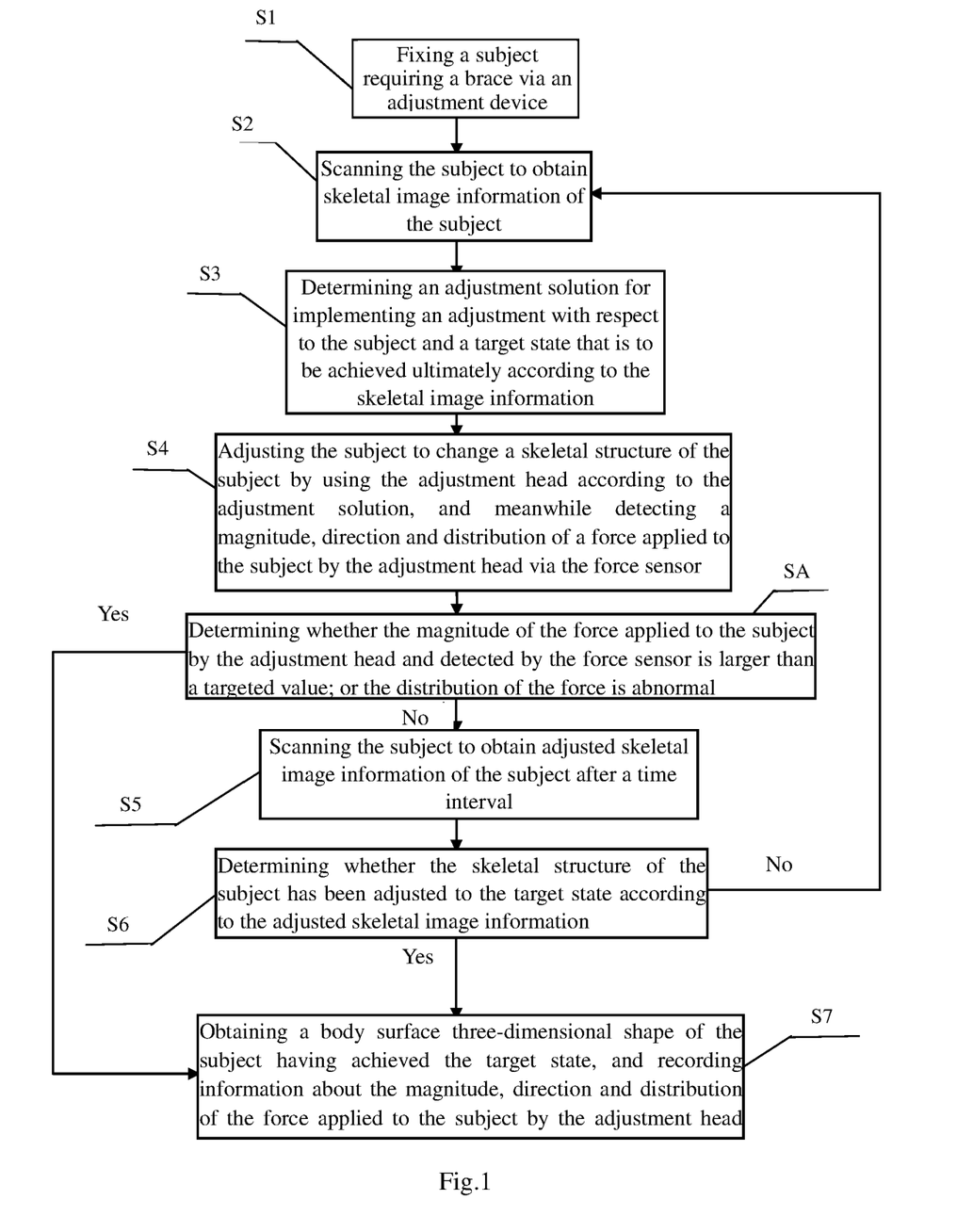
FIG. 1 is a flow chart of the method for a brace designing according to a preferred embodiment of the present application.

FIG. 1 is a flow chart of the method for a brace designing according to a preferred embodiment of the present application, which comprises following steps successively.

In step S1, a subject 2 requiring a brace is fixed via an adjustment device 1. The subject 2 may be a scoliosis which should be controlled by a designed and manufactured brace, or a long bone fracture which should be fixed by a designed and manufactured brace for fixing the broken or deformed long bone to facilitate its healing, or a painful knee joint which needs a designed and manufactured brace for supporting it to relieve the pain. The adjustment device 1 has a plurality of adjustment heads 12 each provided with a force sensor 13 for detecting a magnitude, direction and distribution of a force applied to the subject 2 by the adjustment head 12.

In step S2, the subject 2 is scanned to obtain skeletal image information of the subject 2. In the present embodiment, a non-radiative ultrasonic imaging method is employed for scanning the subject 2 by using a robot to obtain the adjusted skeletal image information. In the other embodiments, the adjusted skeletal image information can also be obtained by a manual scanning or a mechanical scanning of a scanning head held by an operator, or a flexible ultrasonic probe attached on the body surface of the subject 2. The skeletal image information generally refers to a two-dimensional skeletal image or a three-dimensional skeletal image of the subject 2. Of course, in other embodiments, the operator may also employ other known non-radiative imaging methods, such as optical tomography (OCT) imaging methods, photo acoustic imaging methods, terahertz (THz) imaging methods, etc., or ultra-low radiative X-ray imaging method.

In step S3, an adjustment solution for implementing an adjustment with respect to the subject 2 and a target state that is to be achieved ultimately, are determined according to the skeletal image information. When the two-dimensional skeletal image or a three-dimensional skeletal image of the subject 2 are obtained, the operator can obtain the quantitative parameters of the skeletal structure of the subject 2 according to the two-dimensional skeletal image or three-dimensional skeletal image, such as the lateral curvature angle, rotation angle of the bones. The current skeletal structure of the subject 2 is parameterized by detailed analysis and measurement, and the parameters corresponding to the target state after the final adjustment are analyzed and calculated. Accordingly, a corresponding set of adjustment solutions can be formulated, including the position which should be adjusted and the corresponding adjustment amount. It should be noted that when the subject 2 is a scoliosis, the adjusted target state may be adjusting the spine to an ideal state, such as a straight state. Of course, not the spine of every patient with scoliosis can be adjusted to be straight, while most of them can only be adjusted to an optimal state, not a completely straight state. When the subject 2 is a long bone fracture, the adjusted target state is to make the broken bone joint together as much like what they were before as possible. When the subject 2 is the knee joint, the adjusted target state is to guarantee that the painful part of the knee joint is subjected to a force which is as small as possible.

In step S4, the subject 2 is adjusted to change a skeletal structure of the subject 2 by using the adjustment head 12 according to the adjustment solution, and meanwhile the force sensor 13 detects a magnitude, direction and distribution of a force applied to the subject 2 by the adjustment head 12. The operator can operate the plurality of adjustment heads 12 according to the adjustment solution for adjusting the subject 2 accordingly to change the skeleton structure of the subject 2, and approaching the skeletal structure of the subject 2 to the set target state. During the adjustment process, the adjustment head 12 is generally not a point in contact with the subject 2, but a surface that is adjacent to the corresponding portion of the body surface and in contact with the subject 2. When the adjustment head 12 is in contact with the subject 2, the force sensor 13 starts to obtain the magnitude, direction and distribution of the force generated by the adjustment head 12 on the subject 2, and such data is crucial in designing the final brace.

In step SA, whether the magnitude of the force applied to the subject 2 by the adjustment head 12 and detected by the force sensor 13 is larger than a targeted value, or whether the distribution of such force is abnormal, is determined. If yes, that is, the magnitude of the force is larger than the targeted value (safe value) or the distribution of such force is abnormal, the process proceeds to step S7. Or else, that is, the magnitude of the force is not larger than the targeted value and the distribution of such force is normal, the process proceeds to step S5. When the force sensor 13 on the adjustment head 12 detects that the force applied on the body surface of the subject 2 is larger than a certain targeted value, or the stress distribution on the contact surface is abnormal, the adjustment is terminated and the process proceeds to step S7. Or else, the process proceeds to step S5.

In step S5, the subject 2 is scanned to obtain adjusted skeletal image information of the subject 2. After the adjustment of the subject 2 goes through a certain time interval, the operator scans the subject 2 again to obtain the adjusted three-dimensional skeleton image or two-dimensional skeleton image of the subject 2. The time interval may be 30 minutes, 10 minutes, 5 minutes or even a few seconds, depending on the operator's experience.

In step S6, whether the skeletal structure of the subject has been adjusted to the target state is determined according to the adjusted skeleton image information. If yes, the adjustment is terminated and the process proceeds to step S7, or else, the process returns to step S4. The operator can obtain the quantitative parameters of the skeletal structure of the subject 2 which have been adjusted according to the adjusted two-dimensional skeletal image or three-dimensional skeletal image of the subject 2, and compare such quantitative parameters with the parameters corresponding to the target state. If the two of which match with each other, it indicates that the adjustment has already been made completely, then the adjustment is terminated and the process proceeds to step S7. If the two of which never match with each other, it indicates that the adjustment has not already been made completely, then the adjustment is continued and the process returns to step S4.

In step S7, the body surface three-dimensional shape of the subject 2 having achieved the target state is obtained, and the information about the magnitude, direction and distribution of the force applied to the subject 2 by the adjustment head 12 and detected by the force sensor 13 is also recorded for manufacturing a corresponding brace. The operator may employ methods such as traditional plaster bandage, optical body surface 3D imaging, ultrasonic 3D imaging, optical tomography 3D imaging, terahertz 3D imaging, photo acoustic 3D imaging, etc. for obtaining the body surface three-dimensional shape.

Figure 2:
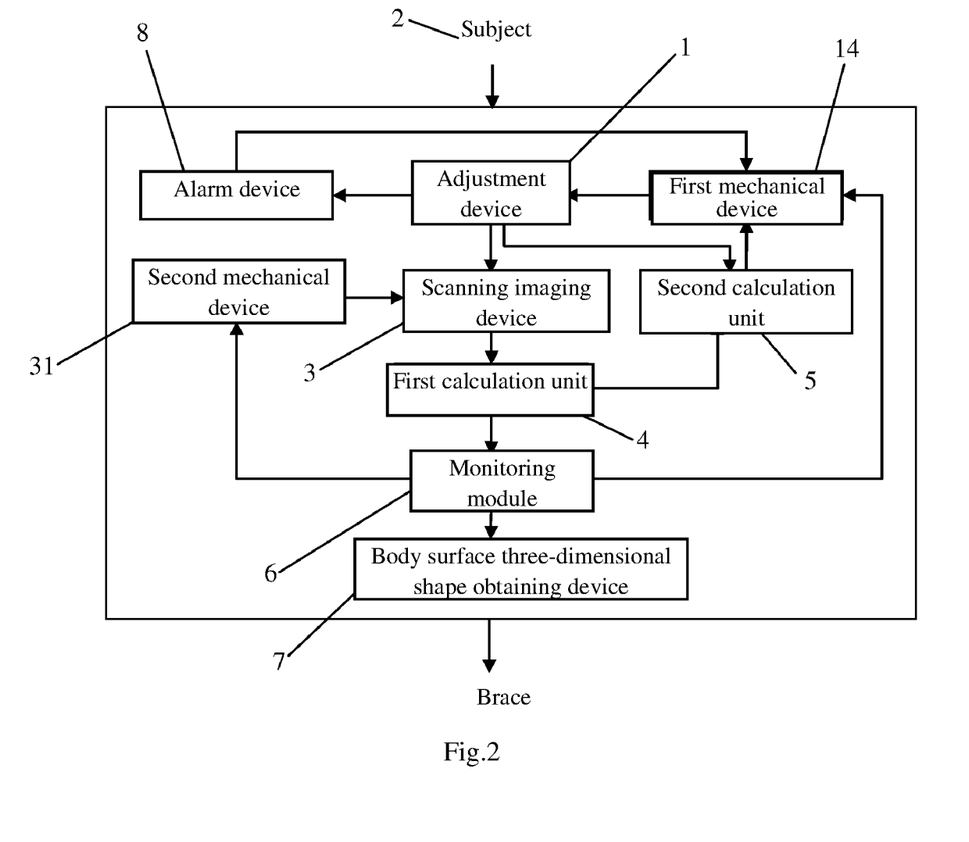
FIG. 2 is a schematic diagram of the system for a brace designing according to a preferred embodiment of the present application.

FIG. 2 is a schematic diagram of the system for a brace designing according to a preferred embodiment of the present application, which comprises following components.

Figure 3:
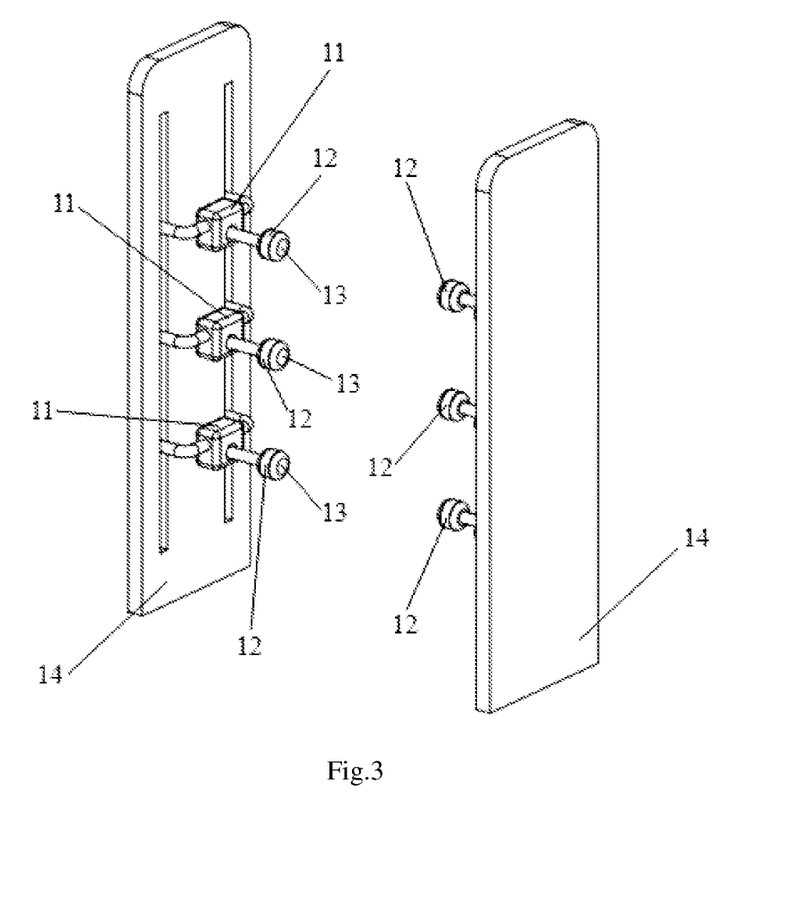
FIG. 3 is a schematic diagram of the adjustment device in the system for a brace designing according to the present application.
Figure 4:
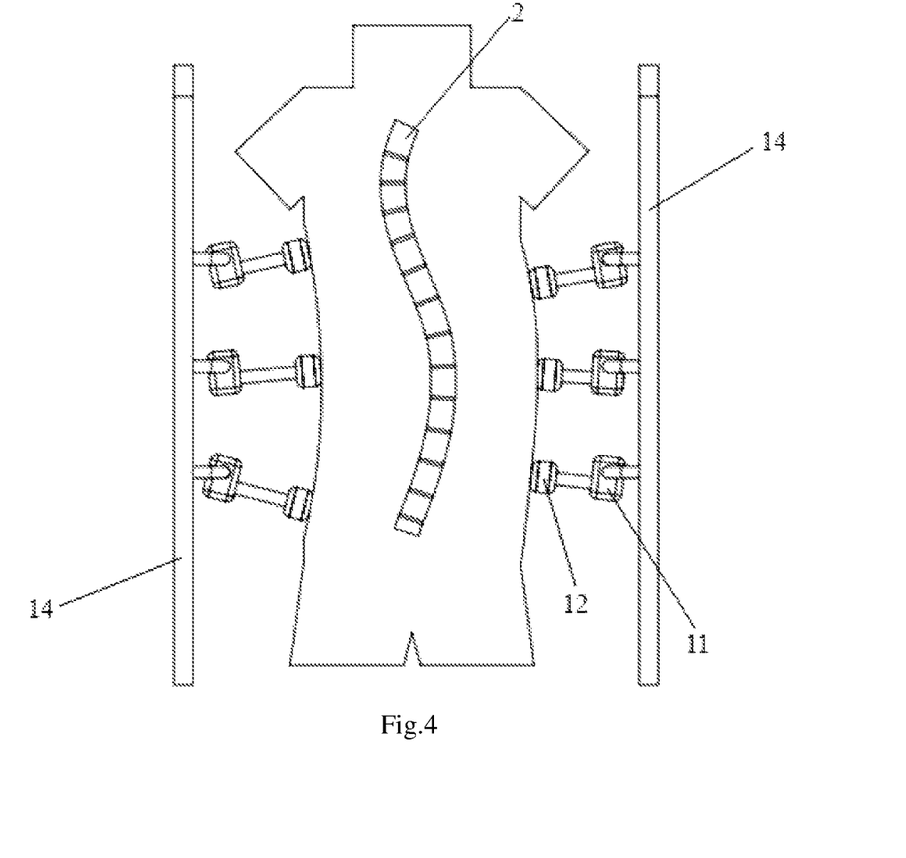
FIG. 4 is an application diagram showing the adjustment of the subject by the system for a brace designing according to a preferred embodiment of the present application.
Figure 5:
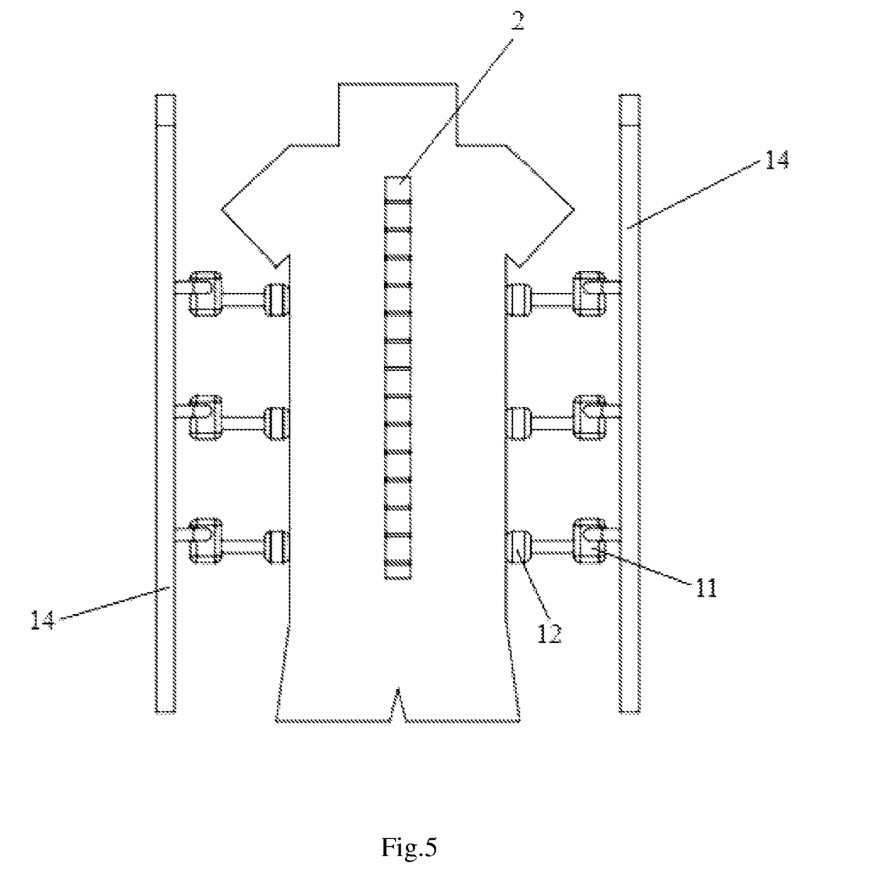
FIG. 5 is an effect diagram showing the subject adjusted by the system for a brace designing according to a preferred embodiment of the present application.

Referring FIGS. 3-5, an adjustment device 1 for fixing a subject 2 requiring a brace is shown. The subject 2 may be a scoliosis which should be controlled by a designed and manufactured brace, or a long bone fracture which should be fixed by a designed and manufactured brace for fixing the broken or deformed long bone to facilitate its healing, or a painful knee joint which needs a designed and manufactured brace for supporting it to relieve the pain. The adjustment device 1 comprises two oppositely arranged fixing frames 14, and a plurality of adjustment heads 12 respectively mounted on the fixing frames 14. The adjustment heads 12 can be moved upwardly, downwardly, forwardly, backwardly, left, right, and even rotated various angles. The adjustment heads 12 is controlled by the first mechanical device 11 having a first numerical control module and a brake module. Each adjustment head 12 is provided with a force sensor 13 for detecting a magnitude, direction and distribution of a force applied to the subject 2 by the adjustment head 12.

An alarm device for reading information about the magnitude of the force applied to the subject 2 by the adjustment head 12 and detected by the force sensor 13 is also provided. When the magnitude of the force applied to the subject 2 by the adjustment head 12 is larger than the safe value, or the distribution of such force is abnormal, the alarm device sends out an alarm signal. The brake module of the first mechanical device 11 receives such alarm signal and sends out a termination signal to stop the running of the first mechanical device 11.

A scanning imaging device 3 for scanning the subject 2 in real time to obtain the real-time two-dimension skeletal image or three-dimensional skeletal image of the subject 2. In the present embodiment, the scanning imaging device 3 is a non-radiative ultrasonic imaging device, which is controlled by a second mechanical device 31. In the other embodiments, the skeletal image can also be obtained by a manual scanning or a mechanical scanning of a scanning head held by an operator. The second mechanical device 31 has a second numerical control module. Of course, in other embodiments, other known non-radiative imaging device can be employed, such as an optical tomography (OCT) imaging device, a photo acoustic imaging device, a terahertz (THz) imaging device, etc., or a ultra-low radiative X-ray imaging device.

A first calculation unit 4 is further provided for reading the two-dimension skeletal image or three-dimensional skeletal image of the subject 2 and then calculating the current parameter of the skeletal structure of the subject 2, such as lateral curvature angle, rotation angle of the bones, and meanwhile calculating the target parameters corresponding to the target state of the bones of the subject 2 after the final adjustment. It should be noted that when the subject 2 is a scoliosis, the adjusted target state may be adjusting the spine to an ideal state, such as a straight state. Of course, not the spine of every patient with scoliosis can be adjusted to be straight, while most of them can only be adjusted to an optimal state, not a completely straight state. When the subject 2 is a long bone fracture, the adjusted target state is to make the broken bone joint together as much like what they are before as possible. When the subject 2 is the knee joint, the adjusted target state is to guarantee that the painful part of the knee joint is subjected to a force which is as small as possible.

A second calculation unit 5 is further provided for reading the current parameter, the target parameter and the magnitude, direction and distribution of the force applied to the subject 2 by the adjustment head 12 and detected by the force sensor 13, and calculating an adjustment solution which adapts to the subject 2 and comprises the position which should be adjusted and the corresponding adjustment amount.

A monitoring module 6 is provided for monitoring whether the current parameter is consistent with the target parameter. If yes, a termination signal is sent out, or else an operation signal is sent out.

When the operation signal sent out by the monitoring module 6 is received by the first numerical control module, the first mechanical device 11 reads the adjustment solution calculated by the second calculation unit 5 and controls the adjustment head 12 to adjust the subject 2 according to the adjustment solution. When the operation signal sent out by the monitoring module 6 is received by the second numerical control module, the second mechanical device 31 controls the scanning imaging device to scan the subject 2 for obtaining the skeletal image information of the subject 2.

When the termination signal sent out by the monitoring module 6 is received by the first numerical control module, the first mechanical device 11 stops running. When the termination signal sent out by the monitoring module 6 is received by the second numerical control module, the second mechanical device stops running. Then the operator can obtain the body surface three-dimensional shape of the subject 2 by a body surface three-dimensional shape obtaining device 7 which obtains the body surface three-dimensional shape of the subject 2 by obtaining a cross-sectional view of the subject 2 and a spatial position of each cross-sectional view. In other embodiments, the body surface three-dimensional shape obtaining device 7 can be provided with a third numerical control module for receiving signals sent out by the monitoring module 6. When the third numerical control module receives the termination signal, the body surface three-dimensional shape obtaining device 7 starts running. When the third numerical control module receives the operation signal, the body surface three-dimensional shape obtaining device 7 stops running.

Therefore, the adjustment of the subject 2 can form a closed loop automatic adjustment process, that is, to continuously obtain a three-dimensional skeleton image or two-dimensional skeleton image of the subject 2, calculate the current parameters, and approach the current parameter to the target parameter by the corresponding adjustment of the plurality of adjustment heads 12 until the current parameter is consistent with the target parameter, such that the entire adjustment process can be completed completely automatically.

In other embodiments, the preferred embodiment of the system for a brace designing further includes a set of emergency braking devices including a power switch and a mechanical switch for safety reasons. The power switch is used to control all the adjustment heads 12. In an emergency, the power switch can be activated to stop all the adjustment heads 12, thereby ensuring the personal safety of the subject 2. The mechanical switch can mechanically control all of the adjustment heads 12 to be locked or away from the subject 2 for a distance instantaneously, thereby ensuring the personal safety of the subject 2 even in the event of failure of the power switch. It should be noted that the power switch and the mechanical switch can be controlled by the operator or the patient himself.

In other embodiments, in order to make more effective adjustments, the first mechanical device 11 is further provided with a memory unit for storing an adjustment scheme for each case, and the second calculation unit 5 can read the adjustment scheme of the previous case in the memory unit for reference, so that the adjustment scheme of the current subject 2 can be calculated and optimized faster and better. With more and more cases, the calculation and optimization of adjustment scheme is becoming easier.

When implementing the method and system for a brace designing according to the present application, following beneficial effects can be obtained.

1. The brace suitable for the corresponding subject 2 can be designed efficiently and intelligently for the different subjects 2, and the designed brace can both ensure a good orthopedic effect and avoid continuous skin compression, thus seeking a valuable treatment time and ideal treatment effect for the patients.

2. During the entire design of the brace, the radiation to the subject 2 is almost zero, which can guarantee the personal safety of the subject.

The embodiments of the present application have been described above with reference to the drawings, but the present application is not limited to the specific embodiments described above, and the specific embodiments described above are merely illustrative and not restrictive, and those skilled in the art In the light of the present application, many forms may be made without departing from the spirit and scope of the application as claimed.

What is claimed is:

1. A method for brace designing comprising following steps:
    S1, placing an adjustment device comprising one or more adjustment head provided with a force sensor on a subject wearing a brace, wherein the subject stands still when wearing the brace;
    S2, scanning the subject to obtain skeletal image information of the subject;
    S3, determining an adjustment solution for implementing an adjustment with respect to the subject and a target state that is to be achieved ultimately according to the skeletal image information, wherein when a two-dimensional skeletal image or a three-dimensional skeletal image of the subject are obtained, an operator obtains quantitative parameters of a skeletal structure of the subject according to the two-dimensional skeletal image or three-dimensional skeletal image, wherein the quantitative parameters comprises a lateral curvature angle and a rotation angle of bones; current skeletal structure of the subject is parameterized by analysis and measurement, and parameters corresponding to the target state are analyzed and calculated;

S4, adjusting the subject to change skeletal structure of the subject by using the adjustment head according to the adjustment solution, and meanwhile detecting a magnitude, direction and distribution of a force applied to the subject by the adjustment head via the force sensor, wherein the plurality of adjustment heads is operated according to the adjustment solution for adjusting the subject accordingly to change the skeleton structure of the subject and approaching the skeletal structure of the subject to the target state, wherein during the adjustment process, the adjustment head is a surface that is adjacent to corresponding portion of a body surface and in contact with the subject, wherein when the adjustment head is in contact with the subject, the force sensor starts to obtain the magnitude, direction and distribution of the force generated by the adjustment head on the subject;

SA, determining whether the magnitude of the force applied to the subject by the adjustment head and detected by the force sensor is larger than a targeted value or whether a distribution of such force is abnormal; if yes, terminating the adjustment and proceeding to step S7, or else, proceeding to step S5;

S5, scanning the subject to obtain adjusted skeletal image information of the subject after an adjustment of the subject goes through a certain time interval;

S6, determining whether the skeletal structure of the subject has been adjusted to the target state according to the adjusted skeletal image information; if yes, terminating adjustment and proceeding to step S7, or else, returning to step S4, wherein in step S6, the operator obtains quantitative parameters of the skeletal structure of the subject which have been adjusted according to the adjusted two-dimensional skeletal image or three-dimensional skeletal image of the subject, and compares such quantitative parameters with the parameters corresponding to the target state, if the two of which match with each other, it indicates that the adjustment has already been made completely, then the adjustment is terminated and the process proceeds to step S7; if the two of which do not match with each other, it indicates that the adjustment has not already been made completely, then the adjustment is continued and the process returns to step S4;

S7, obtaining a body surface three-dimensional shape of the subject having achieved the target state, and recording information about the magnitude, direction and distribution of the force applied to the subject by the adjustment head and detected by the force sensor for manufacturing a corresponding brace.

2. The method for brace designing according claim 1, wherein the skeletal image information in step S2 is displayed in real time for giving reference to step S3.

3. A system for brace designing comprising:
an adjustment device placed on a subject wearing a brace, wherein the subject stands still when wearing the brace;
wherein the adjustment device comprises one or more adjustment head provided with a force sensor for detecting a magnitude, direction and distribution of a force applied to the subject by the adjustment head;
a scanning imaging device for scanning the subject to obtain skeletal image information of the subject;
a first processor for reading, quantizing and calculating the skeletal image information for obtaining a corresponding current parameter and target parameter of the subject;
a second processor for calculating an adjustment solution of the adjustment head for guiding an operator to adjust the subject by using the adjustment head, according to the current parameter, the target parameter, the magnitude, direction and distribution of the force applied to the subject by the adjustment head and detected by the force sensor;
a comparator or processor for comparing whether the current parameter is consistent with the target parameter; if yes, sending out a termination signal to prompt the operator to terminate the adjustment and obtain the body surface three-dimensional shape of the subject by using a body surface three-dimensional shape obtaining device, or else sending out an operation signal to prompt the operator to continue the adjustment;
an alarm device for reading information about the magnitude of the force applied to the subject by the adjustment head and detected by the force sensor, and sending out an alarm signal to prompt the operator to terminate the adjustment when the magnitude of the force applied to the subject by the adjustment head and detected by the force sensor is larger than a targeted value or a distribution of such force is abnormal;
wherein the plurality of adjustment heads is operated according to the adjustment solution for adjusting the subject accordingly to change the skeleton structure of the subject and approaching the skeletal structure of the subject to a target state, wherein during the adjustment process, the adjustment head is a surface that is adjacent to corresponding portion of a body surface and in contact with the subject, wherein when the adjustment head is in contact with the subject, the force sensor starts to obtain the magnitude, direction and distribution of the force generated by the adjustment head on the subject;
wherein when a two-dimensional skeletal image or a three-dimensional skeletal image of the subject are obtained, the operator obtains quantitative parameters of a skeletal structure of the subject according to the two-dimensional skeletal image or three-dimensional skeletal image, wherein the quantitative parameters comprises a lateral curvature angle and a rotation angle of bones; current skeletal structure of the subject is parameterized by analysis and measurement, and parameters corresponding to the target state are analyzed and calculated; then the operator compares such quantitative parameters with the parameters corresponding to the target state, if the two of which match with each other, it indicates that the adjustment has already been made completely, then the adjustment is terminated; if the two of which do not match with each other, it indicates that the adjustment has not already been made completely, then the adjustment is continued.

4. The system for brace designing according to claim 3, wherein the adjustment head is controlled by a first mechanical device having a brake module for receiving the alarm signal, wherein the first mechanical device stops running when the brake module receives the alarm signal.

5. The system for brace designing according to claim 4, wherein the first mechanical device has a first numerical control module for receiving signals sent by the monitoring module, wherein when the first numerical control module receives the termination signal, the first mechanical device stops running, while when the first numerical control module receives the operation signal, the first mechanical device reads the adjustment solution calculated by the second calculation unit and controls the adjustment head to adjust the subject according to the adjustment solution.

6. The system for brace designing according to claim 3, wherein the scanning imaging device is controlled by a second mechanical device comprising a second numerical control module for receiving signals sent by the monitoring module; wherein when the second numerical control module receives a termination signal, the scanning imaging device stops running, while when the second numerical control module receives an operation signal, the second mechanical device controls the scanning imaging device to scan the subject for obtaining the skeletal image information of the subject.

7. The system for brace designing according to claim 3, wherein the body surface three-dimensional shape obtaining device obtains the body surface three-dimensional shape of the subject by obtaining a cross-sectional view of the subject and a spatial position of each cross-sectional view.

8. The system for brace designing according to claim 3, wherein the scanning imaging device comprises a flexible imaging probe attached to a body surface of the subject.

* * * * *